United States Patent [19]

Hötzel

[11] Patent Number: 5,524,472
[45] Date of Patent: Jun. 11, 1996

[54] EVALUATING ARRANGEMENT FOR THE SIGNAL OF AN OXYGEN PROBE

[75] Inventor: Gerhard Hötzel, Stuttgart, Germany

[73] Assignee: Robert Bosch GmbH, Stuttgart, Germany

[21] Appl. No.: 363,618

[22] Filed: Dec. 23, 1994

[30] Foreign Application Priority Data

Dec. 30, 1993 [DE] Germany ............... 43 44 961.1

[51] Int. Cl.$^6$ ..................... G01N 27/416; F01N 9/00
[52] U.S. Cl. ............................. 73/1 G; 73/23.32
[58] Field of Search ..................... 73/1 G, 23.32; 204/406; 123/694, 696, 697

[56] References Cited

U.S. PATENT DOCUMENTS

| | | |
|---|---|---|
| 4,419,190 | 12/1983 | Dietz et al. . |
| 4,626,338 | 12/1986 | Kondo et al. . |
| 4,708,777 | 11/1987 | Kuraoka . |
| 4,753,203 | 6/1988 | Yamada ................. 73/23.32 |
| 4,938,196 | 7/1990 | Hoshi et al. ............. 123/697 |
| 5,111,792 | 5/1992 | Nagai et al. ............. 123/697 |
| 5,140,535 | 8/1992 | Raff et al. ............... 123/694 |
| 5,218,946 | 6/1993 | Wild et al. .............. 123/697 |

FOREIGN PATENT DOCUMENTS

| | | |
|---|---|---|
| 3840248 | 6/1989 | Germany . |
| 3842287 | 8/1989 | Germany ............... 123/697 |
| 12855 | 1/1988 | Japan .................... 123/694 |
| 148856 | 5/1992 | Japan ................... 123/23.32 |

Primary Examiner—Hezron E. Williams
Assistant Examiner—Daniel S. Larkin
Attorney, Agent, or Firm—Walter Ottesen

[57] ABSTRACT

The invention is directed to an evaluating arrangement 10 for the probe signal of a heated amperometric oxygen probe 11 which is mounted in the flow of the exhaust gas from an internal combustion engine 13. The heater unit 18 of the probe is continuously operated with such a heater voltage that the internal resistance of the prove remains constant. However, for this reason, an ever increasing probe temperature (that is, an however, leads to an unwanted increase of the probe signal and this increase must be compensated. For this compensation, the realization is utilized that the increase of the probe temperature is clearly connected to the increase of the heater voltage. The amount of the increase of the heater voltage is determined by comparison measurements in a calibration operating state of the engine. A corrective value is formed from the detected change of the heater voltage and is mathematically coupled to the measurement signal in order to obtain a corrected measurement signal which exhibits neither temperature-caused errors nor deterioration-caused errors.

2 Claims, 2 Drawing Sheets

EVALUATING ARRANGEMENT FOR THE SIGNAL OF AN OXYGEN PROBE

FIELD OF THE INVENTION

The invention relates to an evaluating arrangement for the probe signal of an amperometric oxygen probe which is mounted in the flow of the exhaust gas of an internal combustion engine.

BACKGROUND OF THE INVENTION

The limit-current oxygen probe will be, for tile sake of brevity, referred to in the following as simply an oxygen probe. The function of the oxygen probe for measuring the oxygen content of a lean mixture will be explained below with respect to FIG. 5.

In FIG. 5, the pump current ip is shown plotted as a function of the pump voltage Up at a pregiven operating temperature. This operating temperature can, for example, be 850° C. with the ohmic internal resistance of the probe being 100 Ω. As soon as tile pump voltage is applied to the probe, $O_2$ molecules, which are entrained in the exhaust gas penetrating into the diffusion space of the cell, are reduced to $O^{2-}$ ions. These $O^{2-}$ ions are pumped through the electric field applied to the probe material and out of the diffusion space. For low pump voltages, tile current is limited only by the ohmic resistance. For this reason, the ip-Up characteristic is at first linear. However, when only very few $O_2$ molecules are in the exhaust gas, then a saturation of the pump current occurs already at relatively low pump voltages. This is shown in FIG. 5 by the solid line which occupies the lowest position in this graph. The higher the saturation level is, the leaner is the mixture.

The pump voltage is typically pregiven with such a great value that the pump current is in the saturation range for actual use of such a probe in the flow of the exhaust gas of an internal combustion engine. In this way, this current is a direct measure for the oxygen content of the exhaust gas penetrating into the diffusion space of the probe. For the sake of completeness, it should be noted that measurement methods also exist which vary the pump voltage in dependence upon the oxygen content, namely, the lower the oxygen present, the lower the pump voltage. From FIG. 5, it can be seen directly that for lower quantities of oxygen, lower pump voltages can be used, but the condition is still satisfied that measurements are made in the saturation region of the characteristic. For the invention, it is insignificant whether the pump voltage is held constant or is varied in dependence upon oxygen content.

The characteristics shown in FIG. 5 by the solid lines apply to a probe newly placed into service. However, the internal resistance of a probe increases with increasing deterioration. To provide an overview in FIG. 5, it is assumed that the internal resistance after long service is only half of the internal resistance at the start of use with the temperature being the same in each case. As shown by the broken line in FIG. 5, the pump current is greatly limited by ohmic resistance and the pump current still does not reach its saturation for a very lean mixture for the pump voltage, which is applied in the practical application and is shown in FIG. 5 by a vertical line. Accordingly, the limit current is not measured which is determined by the actual oxygen concentration; instead, a lower current is measured which means that the oxygen concentration is incorrectly measured. In order to prevent this, the probe is controlled to a constant internal resistance of the electrochemical cell. In this way, the slope of the described characteristic is maintained even during deterioration of the probe but the probe temperature increases with increasing probe deterioration.

In addition to internal resistance, the magnitude of the output signal of a probe is, however, also greatly dependent upon temperature because the diffusion conditions differ greatly with temperature. In order to exclude measurement errors caused by temperature, it is known to control the temperature so that the probe temperature is constant. This control is effected via a measurement of the internal resistance of the probe's heater (U.S. Pat. No. 4,708,777). It is also known to measure the probe's temperature and to correct the measurement signal of the probe, which indicates the oxygen content, with the aid of the measured temperature (German patent publication 3,840,248).

The foregoing applies essentially also to two-cell oxygen probes wherein $O^{-2}$ ions are pumped out of a diffusion space or into this diffusion space via a pump cell in order to measure a lean or rich mixture. The pumping takes place in such a manner that a second cell, the sensor cell, always shows a pregiven constant voltage. With deterioration, such a probe also shows an increase of the internal resistance with the danger that the pump voltage which is available is no longer adequate to carry out the total actually required $O^{-2}$ transport. This difficulty can be avoided when a constant internal resistance is adjusted; however, then here too the problem of incorrect measurement occurs because of temperature increase.

The invention is directed to amperometric oxygen probes and these probes include single-cell and two-cell oxygen probes having the above-described functions.

SUMMARY OF THE INVENTION

It is an object of the invention to provide an evaluating arrangement for the probe signal of a heated amperometric oxygen probe which is mounted in the flow of the exhaust gas of an internal combustion engine which can compensate for measurement errors of the probe signal caused by deterioration so that even a deteriorated probe can still be utilized without an increase of the toxic gas output.

The evaluating arrangement of the invention is characterized in that it repeatedly carries out a recalibration measurement for a pregiven operating state of the internal combustion engine in order to compensate, with the aid of a corrective value, for changes of the probe signal caused by deterioration. It is especially important that there always be a control to the constant internal resistance of the probe (not of the heater) and that the heater voltage is used as a measure for the state of the deterioration of the probe. The heater voltage here is required for the above-mentioned pregiven operating state. This procedure leads to the condition that, with increasing deterioration of the probe, the probe is heated with increasing intensity in order to maintain its internal resistance constant which, on the one hand, causes the measurement signal not to be adulterated by a change of the internal resistance but, on the other hand, that the measurement signal is caused to have a temperature-caused error. However, the temperature-caused error can be derived with great precision from the change of the heater voltage so that this error can be very easily compensated without it being necessary to provide a temperature sensor for this purpose.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
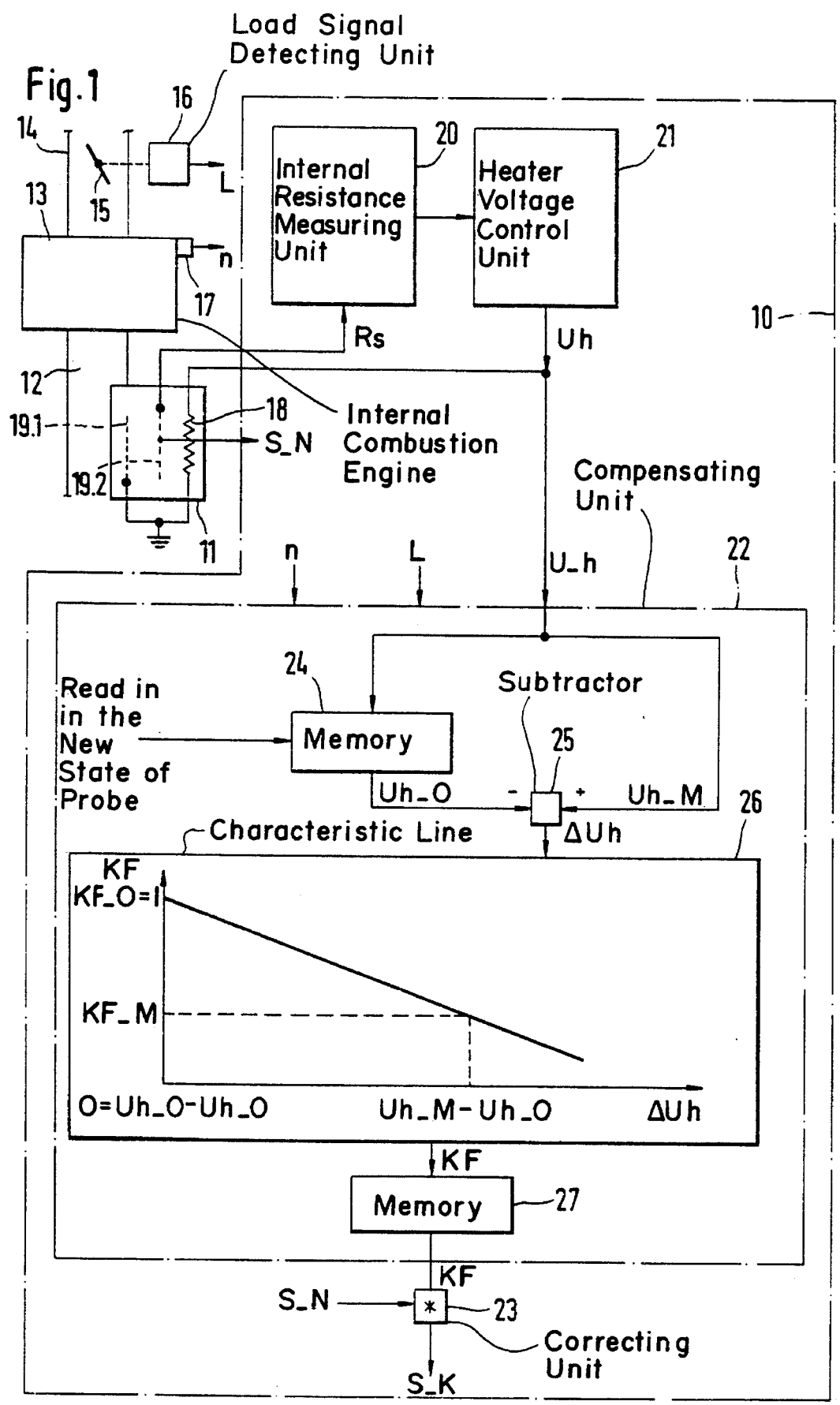
FIG. 1 is a block function diagram of an evaluating arrangement with deterioration compensation for the probe signal of a heated limit-current oxygen probe.

FIG. 1 shows an evaluating arrangement 10 for the probe signal of a heated limit-current oxygen probe 11 which is mounted in the exhaust gas pipe 12 of an internal combustion engine 13. A throttle flap 15 is mounted in the intake pipe 14 of the engine. A load-signal detecting device 16 is mounted on the throttle flap and provides a load signal L. A rpm sensor 17 on the engine supplies a rpm signal (n).

The probe 11 is shown only schematically with a heater device 18 as well as two measuring electrodes 19.1 and 19.2. The above-mentioned pump voltage Up is applied across the two measuring electrodes 19.1 and 19.2 through which the pump current ip flows. The probe signal outputted by the probe 11 is identified as S_N and is not corrected for deterioration.

The evaluating arrangement 10 according to FIG. 1 includes an internal resistance measuring unit 20, a heater voltage control unit 21, a compensating unit 22, and correcting unit 23 in the form of a multiplier. The compensating unit 22 is, in turn, made up of a new-state value memory 24, a subtractor 25, a characteristic line 26, and a corrective value memory 27.

The internal resistance measuring unit 20 measures the internal resistance Rs of the probe 11 in that it applies an alternating voltage in the range of, for example, 1 to 5 kHz across the probe electrodes 19.1 and 19.2. The internal resistance measuring unit 20 outputs the measured resistance value to the heater-voltage control unit 21 where this value is compared to a desired value for the probe internal resistance of, for example, 100 Ω. The heater-voltage control unit outputs such a heater voltage Uh that the measured probe internal resistance is held as close to the desired value as possible.

The probe's internal resistance Rs continuously increases with increasing probe deterioration at a specific temperature of, for example, 850° C. but, on the other hand, the probe internal resistance Rs drops with increasing temperature. For this reason, holding the probe's internal resistance constant with the aid of the heater-voltage control unit 21 means that the probe's temperature continuously increases the older the probe becomes. With increasing probe temperature, however, the non-corrected probe signal S_N becomes increasingly adulterated. This adulteration must be compensated and, for this purpose, the heater voltage Uh is used as it must be applied at specific operating states of the engine so that the internal resistance of the probe assumes its desired value. This compensation is carried out by the compensating unit 22 in the manner described below.

After first taking the motor vehicle into service, a deterioration calibration is carried out as soon as a pregiven calibration operating state of the engine adjusts, for example, an idle or overrun operation. It must be an operating state for which the probe 11 assumes a temperature in a very narrow temperature range with the probe's heater switched off. This narrow temperature range can, for example, be 700° C. with a deviation of only a few degrees. The heater voltage Uh (as it must be set in order to obtain a pregiven internal resistance of the probe) is then a measure for the deterioration of the probe. For the new state of the probe, this voltage is, for example, 9 V and a temperature of 850° C. is obtained in order to reach the pregiven internal resistance of, for example, 100 Ω. This voltage Uh_ O is stored in the memory 24 as a new-state value.

During later actual operation of the motor vehicle, the calibrating operation then takes place each time when the engine reaches the calibration operating state. The older the probe becomes, the higher the temperature is which is required in order to obtain the probe's pregiven internal resistance of 100 Ω. Since the engine always supplies the same heat quantity in the calibration operating state, the heat quantity which is required to obtain the higher temperature, must be developed entirely from the heater unit 18 by applying a higher heater voltage Uh.

The heater voltage Uh_ M which is measured in an actual calibrating procedure, is a value which indicates the instantaneous state of the probe. The new-state value Uh-O stored in the memory unit 24 is subtracted from this voltage. With the aid of this difference, a corrective factor KF=KF_ M is read out of the characteristic line 26 with which the non-corrected probe signal S_ N is multiplied in the multiplier unit 23 in order to obtain a corrected probe signal S_ K. The instantaneous value KF_ M of the corrective factor KF is always less than 1, which is the value of the corrective factor KF_ O at the new state, because the probe's voltage must be increased with increasing deterioration of the probe in order to obtain the pregiven internal resistance and since with increasing probe voltage and therefore increasing probe temperature, the value of the probe signal increases at constant oxygen concentration. The non-corrected probe's signal is therefore reduced by the corrective factor.

Figures 2, 3, 4:
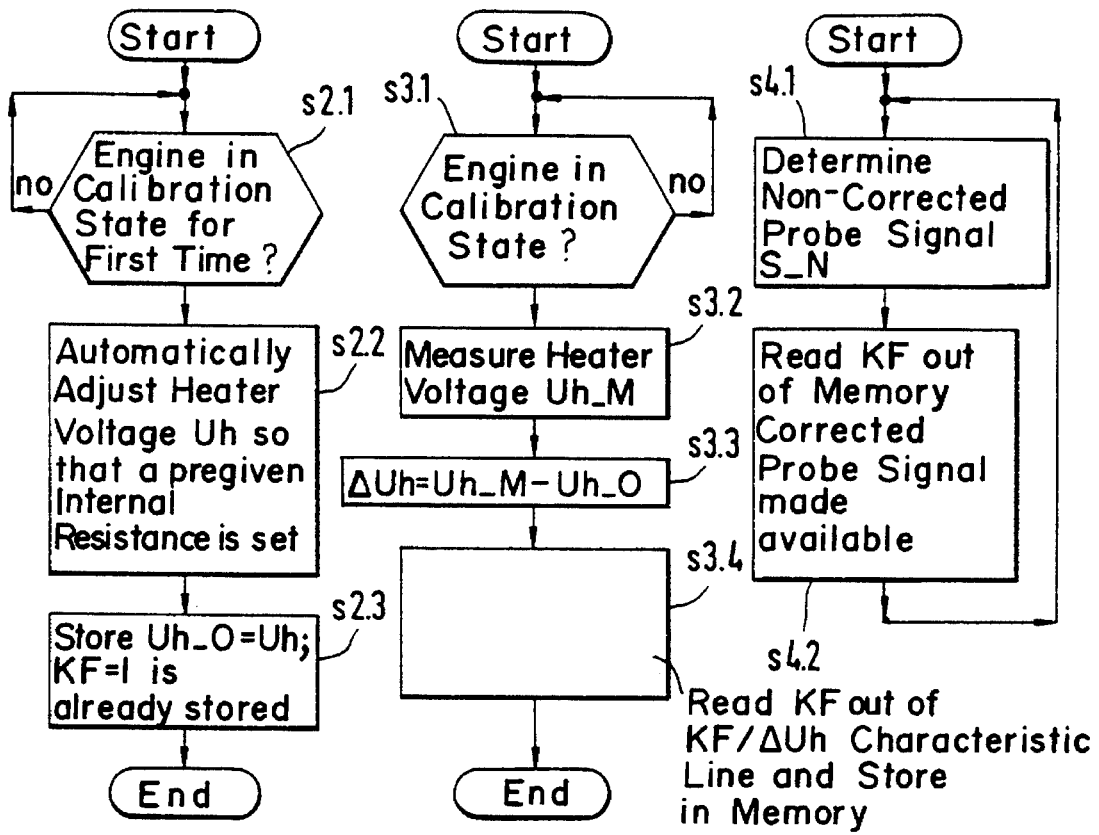
FIG. 2 is a flowchart for explaining the procedure presented in FIG. 1 for determining a value indicating the new state of a probe.
FIG. 3 is a flowchart for explaining a procedure for detecting the state of deterioration of a probe.
FIG. 4 is a flowchart for explaining a procedure for correcting the measuring signal of a probe while utilizing the values detected with the sequences according to FIGS. 2 and 3; and, FIG. 5 is a graph showing the known diagram of pump current plotted as a function of pump voltage for a limit-current oxygen probe.
Figure 5:
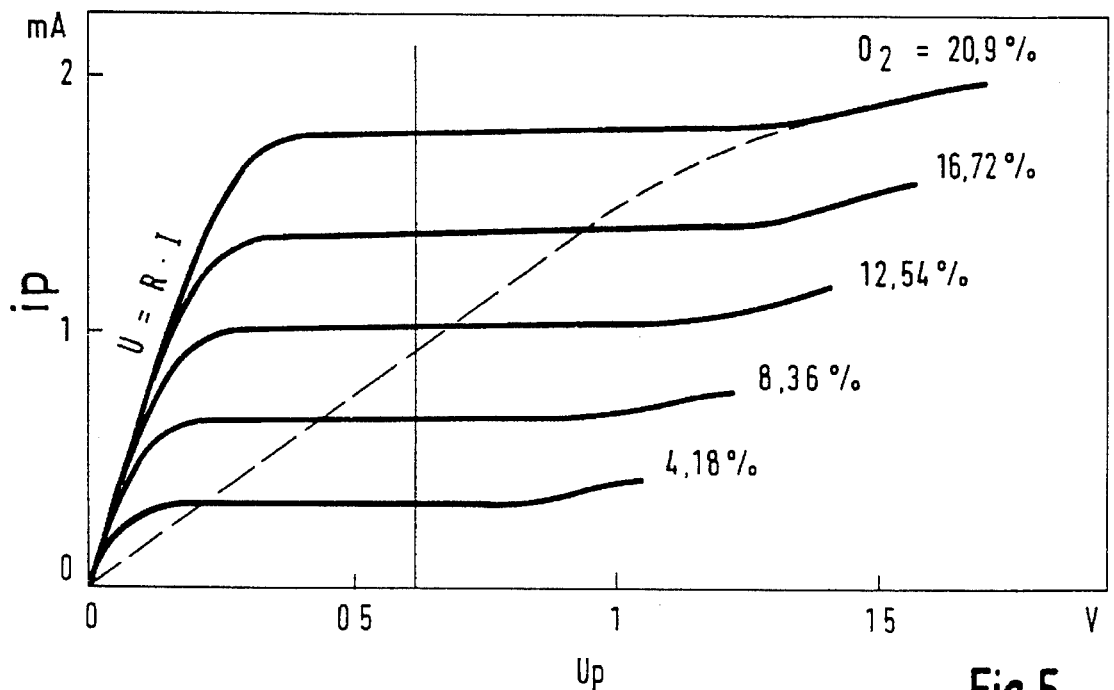

The above-described sequences are now explained with respect to FIGS. 2 to 4.

According to FIG. 2, and after the motor vehicle is taken into service, a check is continuously made in step s2.1 as to whether the engine is driven for the first time in the calibration operating state. As soon as this is the case, the new-state value Uh_ O is measured in step s2.2 wherein the probe's pregiven internal resistance is adjusted. This value is stored in step s2.3. The value 1 for the corrective factor KF is already stored in the corrective factor memory 27.

During later operation of the motor vehicle, a continuous check is made in step s3.1 as to whether the engine has reached the calibration operating state. This is determined in that the actual values of the load signal L and the rpm (n) are compared to pregiven value ranges and when the actual values both lie in the respective value ranges corresponding thereto, this is a sign that the calibration operating state is present. As soon as this is the case, in step s3.2, the heater voltage Uh_ M is measured. The heater voltage control unit 21 runs unchanged as in the non-calibrated operation; that is, tile control unit 21 always runs so that the probe's internal resistance is maintained. In step s3.3, the new state value Oh_ O is subtracted from the instantaneous state value Uh_ M and, in step s3.4, the corrective factor KF corresponding to this difference is read out of the characteristic line 26 and stored in the memory 27.

When operating the engine in operating states other than the calibration operating state, the non-corrected probe signal S_ N is detected for the probe's pregiven internal resistance in step s4.1. In step s4.2, the corrective factor KF is read out of the corrective factor memory 27 and multiplied in multiplier 23 by the non-corrected probe signal. In this way, the corrected probe signal S_ K is provided.

The above-described assembly is especially advantageous when an essentially linear relationship exists between the change of the heater voltage and the change of the probe signal at constant oxygen concentration. If, in contrast, this relationship is non-linear, then it can be more advantageous, in a modified characteristic line, to not record corrective factors as a function of the difference of instantaneous state value minus new-start value, instead, to plot the corrective factors as a function of the percent instantaneous value/new-state value.

In this case, a divider 25 is provided in lieu of the subtractor 25. It is also possible to utilize a characteristic line at the input end of the new start value memory 24 in lieu of a subtractor or divider at the output end. This characteristic line then contains compensating factors plotted directly as a function of the heater voltage and not as a function of a voltage difference or a voltage quotient. A compensating factor is read out and stored from this characteristic line already for the new state. For a later calibration state, a new compensating factor is read out which is divided by the new-state value compensating factor in order to produce the corrective factor KF. Independently of how the corrective factor is specifically determined, it is only important that it corrects that change of the non-corrected probe signal which is produced by a temperature increase which, in turn, is caused by the increase of the heater voltage which, in turn, is necessary in order to compensate for the increase of the probe's internal resistance caused by deterioration.

In the embodiment, a corrective factor is determined, that is, a corrective value, which is multiplicatively coupled to the non-corrected probe signal S_ N. However, it is also possible to determine a corrective summand which is then added to the probe signal. The manner in which the corrective value is determined in each case and in which way it is mathematically coupled to the non-corrected measuring signal is dependent in practice upon the characteristics of the probe and of the total heating system. It is only essential that the probe's internal resistance is continuously held constant and that temperature errors, which are generated because of this measure, are compensated in that the heater-voltage changes are detected which are necessary in order to maintain the internal resistance constant notwithstanding the deterioration of the probe.

The evaluating arrangement according to the invention makes it possible to utilize a limit-current oxygen probe significantly longer than heretofore, notwithstanding deterioration without the use of this probe leading to increased toxic gas emission. However, even in this case, a probe cannot be utilized an unlimited length of time. In order to recognize the time point at which the probe should be exchanged, it can be advantageous to compare the corrective factor to a threshold value. As soon as the corrective factor exceeds the threshold value, then this indicates that an exchange should be made.

It is understood that the foregoing description is that of the preferred embodiments of the invention and that various changes and modifications may be made thereto without departing from the spirit and scope of the invention as defined in the appended claims.

What is claimed is:

1. An evaluating arrangement for a signal of an oxygen probe having a probe heater for amperometrically heating the oxygen probe, the oxygen probe having an internal resistance and being mounted in the flow of exhaust gas from an internal combustion engine, the evaluating arrangement comprising:

probe-signal measuring means for applying a pregiven voltage to said probe to determine a variable in the form of an uncorrected measuring signal (S_ N) indicative of the current flowing through said probe which, in turn, is a measure for the concentration of oxygen in said exhaust gas;

resistance measuring means for determining said internal resistance by applying an alternating voltage to said probe;

control means for driving said probe heater to cause said internal resistance to remain essentially constant;

a compensating device operatively connected to said control means and including:

(a) a memory;

(b) new state determining means for determining a new state value Uh_ O) and reading said new state value (Uh_ O) into said memory;

(c) said new state value (Uh_ O) being a measure for a heater voltage required in the new state of the probe in order to provide said internal resistance for a pregiven calibration operating state of said engine;

(d) instantaneous state value determining means for determining an instantaneous state value (Uh_ M) which is a measure for a heater voltage required in the instantaneous state of said probe in order to obtain said internal resistance for said calibration operating state of said engine; and, (e) corrective value determination means for determining a corrective value (KF) for correcting said measurement signal (S_ N) from a change of said instantaneous state value (Uh_ M) relative to said new state value (Uh_ O); and, corrective means for correcting said uncorrected measurement signal (S_ N) by mathematically coupling said corrective value (KF) to said uncorrected measurement signal. (S_ N) to form a corrected measurement signal (S_ K) .

2. The evaluating arrangement of claim 1, said corrective means being a multiplier unit for multiplying said uncorrected measurement signal (S_ N) by said corrective value (KF).

* * * * *

UNITED STATES PATENT AND TRADEMARK OFFICE
CERTIFICATE OF CORRECTION

PATENT NO. : 5,524,472

DATED : June 11, 1996

INVENTOR(S) : Gerhard Hötzel

It is certified that error appears in the above-identified patent and that said Letters Patent is hereby corrected as shown below:

On the title page, under "ABSTRACT", item [57], line 6: delete "prove" and substitute -- probe -- therefor.

On the title page, under "ABSTRACT", item [57], line 8: Between "an" and "however," insert:
-- ever-increasing heater voltage) is necessary with increasing deterioration of the probe. The higher probe temperature --.

In column 1, line 13: delete "tile" and substitute -- the -- therefor.

In column 1, line 22: delete "tile" and substitute -- the -- therefor.

UNITED STATES PATENT AND TRADEMARK OFFICE
CERTIFICATE OF CORRECTION

PATENT NO. : 5,524,472
DATED : June 11, 1996
INVENTOR(S) : Gerhard Hötzel It is certified that error appears in the above-identified patent and that said Letters Patent is hereby corrected as shown below:

In column 1, line 27: delete "tile" and substitute -- the -- therefor.

In column 4, line 64: delete "tile" and substitute -- the -- therefor.

Signed and Sealed this

Twenty-ninth Day of July, 1997

*Attest:*

*Attesting Officer*

BRUCE LEHMAN

*Commissioner of Patents and Trademarks*